US008317752B2

(12) United States Patent
Cozmi et al.

(10) Patent No.: US 8,317,752 B2
(45) Date of Patent: Nov. 27, 2012

(54) TOUCH SCREEN SYSTEM AND NAVIGATION AND PROGRAMMING METHODS FOR AN INFUSION PUMP

(75) Inventors: Mihaela Cozmi, Gilroy, CA (US); John Arrizza, San Diego, CA (US); John Erik Michael Palmroos, San Diego, CA (US)

(73) Assignee: Hospira, Inc., Lake Forest, IL (US)

( * ) Notice: Subject to any disclaimer, the term of this patent is extended or adjusted under 35 U.S.C. 154(b) by 265 days.

(21) Appl. No.: 12/627,715

(22) Filed: Nov. 30, 2009

(65) Prior Publication Data
US 2010/0100037 A1 Apr. 22, 2010

Related U.S. Application Data

(63) Continuation-in-part of application No. 11/959,330, filed on Dec. 18, 2007, now Pat. No. 7,896,842.

(51) Int. Cl.
*A61M 1/00* (2006.01)
*A61M 37/00* (2006.01)

(52) U.S. Cl. ........................................ 604/151; 604/131

(58) Field of Classification Search .......... 604/151–155, 604/131, 890.1–892.1
See application file for complete search history.

(56) References Cited

U.S. PATENT DOCUMENTS

| 4,756,706 A * | 7/1988 | Kerns et al. ..................... 604/66 |
| 4,898,576 A | 2/1990 | Philip |
| 4,898,578 A | 2/1990 | Rubalcaba, Jr. |
| 5,014,714 A | 5/1991 | Millay et al. |
| 5,041,086 A | 8/1991 | Koenig et al. |
| 5,276,610 A | 1/1994 | Maeda et al. |
| 5,319,363 A | 6/1994 | Welch et al. |
| 5,356,378 A | 10/1994 | Doan |
| D352,778 S | 11/1994 | Irvin et al. |
| 5,406,954 A | 4/1995 | Tomita |
| 5,429,602 A | 7/1995 | Hauser |

(Continued)

FOREIGN PATENT DOCUMENTS

EP 1197178 B1 4/2002

OTHER PUBLICATIONS

Signature Edition GOLD, Alaris Medical Systems Newsletter, date unknown, but believed to be at least as early as Nov. 29, 2008, pp. 70-74 and pp. 2-88 and 2-91, San Diego, CA, USA.

*Primary Examiner* — Nicholas Lucchesi
*Assistant Examiner* — Leah Stohr
(74) *Attorney, Agent, or Firm* — Michael R. Crabb

(57) ABSTRACT

A medical pump system includes an input device for entering a command or a value of a pump programming parameter and a memory for storing a programming code. A processor is in communication with the memory and the input device in order to generate a display signal for an output device to generate one of a plurality of screens, such as near view and far view screens. The programming code is operable to display on a far view screen a plurality of medical therapy buttons that can be used to navigate directly to a near view programming screen. The far view screen can also concurrently display quick titration buttons that are associated with the medical therapy buttons and can be used to navigate directly to a quick titration screen without having to go to a general near view delivery screen or near view programming screen.

17 Claims, 13 Drawing Sheets

U.S. PATENT DOCUMENTS

| | | |
|---|---|---|
| 5,445,621 A | 8/1995 | Poli et al. |
| 5,485,408 A | 1/1996 | Blomquist |
| 5,496,273 A | 3/1996 | Pasterone et al. |
| 5,507,412 A | 4/1996 | Ebert et al. |
| 5,522,798 A | 6/1996 | Johnson et al. |
| 5,547,470 A | 8/1996 | Johnson et al. |
| 5,558,638 A | 9/1996 | Evers et al. |
| 5,609,576 A | 3/1997 | Voss et al. |
| 5,626,151 A | 5/1997 | Linden |
| 5,649,536 A | 7/1997 | Ogura et al. |
| 5,681,285 A | 10/1997 | Ford et al. |
| 5,685,844 A | 11/1997 | Marttila |
| 5,718,562 A | 2/1998 | Lawless et al. |
| 5,743,856 A | 4/1998 | Oka et al. |
| 5,752,919 A | 5/1998 | Schrimpf |
| 5,772,635 A | 6/1998 | Dastur et al. |
| 5,781,442 A | 7/1998 | Engleson et al. |
| 5,782,805 A | 7/1998 | Meinzer et al. |
| 5,792,069 A | 8/1998 | Greenwald et al. |
| 5,803,917 A | 9/1998 | Butterfield et al. |
| 5,814,015 A | 9/1998 | Gargano et al. |
| 5,935,099 A | 8/1999 | Peterson et al. |
| 6,120,459 A | 9/2000 | Nitzan et al. |
| 6,158,965 A | 12/2000 | Butterfield et al. |
| 6,213,972 B1 | 4/2001 | Butterfield et al. |
| 6,241,704 B1 | 6/2001 | Peterson et al. |
| 6,280,391 B1 | 8/2001 | Olson et al. |
| 6,322,516 B1 | 11/2001 | Masuda et al. |
| 6,394,958 B1 | 5/2002 | Bratteli et al. |
| 6,405,076 B1 | 6/2002 | Taylor et al. |
| 6,416,291 B1 | 7/2002 | Butterfield et al. |
| 6,512,944 B1 | 1/2003 | Kovtun et al. |
| 6,544,228 B1 | 4/2003 | Heitmeier |
| 6,641,541 B1 | 11/2003 | Lovett et al. |
| 6,689,069 B2 | 2/2004 | Bratteli et al. |
| 6,731,989 B2 | 5/2004 | Engleson et al. |
| 6,738,052 B1 | 5/2004 | Manke et al. |
| 6,785,573 B2 | 8/2004 | Kovtun et al. |
| 6,801,227 B2 | 10/2004 | Bocionek et al. |
| 6,805,671 B2 | 10/2004 | Stergiopoulos et al. |
| 6,898,301 B2 | 5/2005 | Iwanaga |
| 6,985,768 B2 | 1/2006 | Hemming et al. |
| 6,985,870 B2 | 1/2006 | Martucci et al. |
| 6,997,905 B2 | 2/2006 | Gillespie, Jr. et al. |
| 7,072,725 B2 | 7/2006 | Bristol et al. |
| 7,294,109 B2 | 11/2007 | Lovett et al. |
| 7,668,731 B2 | 2/2010 | Martucci et al. |
| 2001/0044731 A1 | 11/2001 | Coffman et al. |
| 2002/0029776 A1 | 3/2002 | Blomquist |
| 2002/0044059 A1 | 4/2002 | Reeder et al. |
| 2002/0085952 A1 | 7/2002 | Ellingboe et al. |
| 2003/0060765 A1 | 3/2003 | Campbell et al. |
| 2003/0065537 A1 | 4/2003 | Evans |
| 2003/0083583 A1 | 5/2003 | Kovtun et al. |
| 2003/0135087 A1 | 7/2003 | Hickle et al. |
| 2004/0073125 A1 | 4/2004 | Lovett et al. |
| 2004/0193328 A1 | 9/2004 | Zaitsu et al. |
| 2004/0225252 A1 | 11/2004 | Gillespie, Jr. et al. |
| 2005/0145010 A1 | 7/2005 | Vanderveen et al. |
| 2005/0182366 A1 | 8/2005 | Vogt et al. |
| 2006/0042633 A1 | 3/2006 | Bishop et al. |
| 2006/0229557 A1 * | 10/2006 | Fathallah et al. ............ 604/131 |
| 2008/0071580 A1 | 3/2008 | Marcus et al. |
| 2008/0172030 A1 | 7/2008 | Blomquist et al. |
| 2008/0200870 A1 | 8/2008 | Palmeroos et al. |
| 2008/0300572 A1 | 12/2008 | Rankers et al. |
| 2009/0088731 A1 | 4/2009 | Campbell et al. |
| 2009/0131861 A1 | 5/2009 | Braig et al. |
| 2009/0153058 A1 | 6/2009 | Feng et al. |
| 2009/0153463 A1 | 6/2009 | Arrizza et al. |
| 2009/0153595 A1 | 6/2009 | Cozmi et al. |
| 2009/0157432 A1 | 6/2009 | Palmroos et al. |
| 2009/0171289 A1 | 7/2009 | Davis et al. |
| 2009/0177180 A1 | 7/2009 | Rubalcaba, Jr. et al. |
| 2009/0177991 A1 | 7/2009 | Davis et al. |
| 2009/0177992 A1 | 7/2009 | Rubalcaba, Jr. et al. |
| 2009/0183105 A1 | 7/2009 | Teel, IV et al. |
| 2009/0183147 A1 | 7/2009 | Davis |
| 2009/0212966 A1 | 8/2009 | Panduro |

\* cited by examiner

TOUCH SCREEN SYSTEM AND NAVIGATION AND PROGRAMMING METHODS FOR AN INFUSION PUMP

CROSS REFERENCE TO RELATED APPLICATIONS

This application is a continuation-in-part of U.S. patent application Ser. No. 11/959,330 filed Dec. 18, 2007, which claims the benefit of U.S. patent application Ser. No. 11/103,235 filed Apr. 11, 2005; and a continuation-in-part of U.S. patent application Ser. No. 12/337,588 filed Dec. 17, 2008, which claimed priority from U.S. Provisional Patent Application Ser. No. 61/014,677 filed on Dec. 18, 2007.

BACKGROUND OF THE INVENTION

The present invention relates to medical devices. More specifically, the invention relates to infusion pumps that include touch screen graphical user interfaces.

Graphical user interfaces for medical devices that display patient and treatment information have improved clinician efficiency when caring for patients. However, a challenge for designing graphical user interfaces is the need to balance the amount of information displayed on any one screen viewable by the clinician with the need to create a device that is easy to read and navigate. Too often the user is presented with an overwhelming amount of information, impeding the interaction between the user and the user interface.

Additionally, medical devices, including medical pumps, can be complicated and time-consuming for caregivers to program. The need for an improved graphical interface is critical to maintain efficiency of patient care and to reduce potential clinical errors and thereby improve patient safety. Device interfaces that increase input efficiency and accuracy are critical to improve patient safety and therapy.

Graphical user interface design must also take into account strict design parameters as well as safety parameters. As a result, many medical devices do not provide flexibility in programming parameters, neither for the administrator nor for the clinician.

Therefore, it would be desirable to have a medical device that includes a graphical user interface that is easier to navigate, that allows for easier programming of the medical device and that increases efficiency and accuracy of the clinician programming and navigation.

Typically, medical pump systems or medication management systems present two types of screens; a far view screen that is often considered a default screen that is presented when the system is not being actively programmed and a near view screen that is provided when data is being entered into the touch screen. Thus, the near view screen generally presents buttons, fields, and keys that are related to selecting, programming, confirming, starting and stopping a particular infusion therapy. The near view screen provides the user with the means and opportunity to enter the necessary medical data to program the pump to deliver a medical therapy or infusion. Until recently, the far view screen on the other hand has been used merely to indicate an idle or waiting status of the pump or to display in larger text size the status of an on-going infusion therapy. U.S. Patent Publication No. 2009/0183105, a parent of the present application and incorporated in its entirety herein presents and claims the use of a far view screen that utilizes a titration button on the far view screen so that a user quickly gets into and navigates directly to a near view screen, or data entry screen that is associated with the quick titration. However, problems remain. When other data needs to be entered into a near view screen time is wasted going from the far view screen to the near view screen. Specifically, one must still touch the titration button or touch a tab or another spot on the far view screen or go through the menu so that the near view screen can be accessed to start or stop the pump or enter medical data to program the pump.

Therefore, a principal object of the present invention is to provide a medical pump system that has improved programming speed.

Yet another object of the present invention is to provide a medical pump system that allows more efficient work flow for a clinician.

These and other objects, features or advantages will become apparent from the specification and claims.

BRIEF SUMMARY OF THE INVENTION

The medical pump system of this invention has an input device for entering a command or a value of a pump programming parameter. The system additionally has a memory for storing programming code. A processor is in communication with the memory and the input device to generate a display signal. An output device is in communication with the processor and receives the display signal to generate one of a plurality of screens including near view and far view screens. Specifically, the programming code is operable to display a far view screen that has a plurality of buttons that can be used to navigate directly to a titration screen. Other timesaving or useful features and navigation or programming methods are also disclosed.

DETAILED DESCRIPTION OF THE PREFERRED EMBODIMENT

The present invention will be described as it applies to its preferred embodiment. It is not intended that the present invention be limited to the preferred embodiment. It is intended that the invention cover all modifications and alternatives that may be included within the scope of the appended claims.

Figure 1:
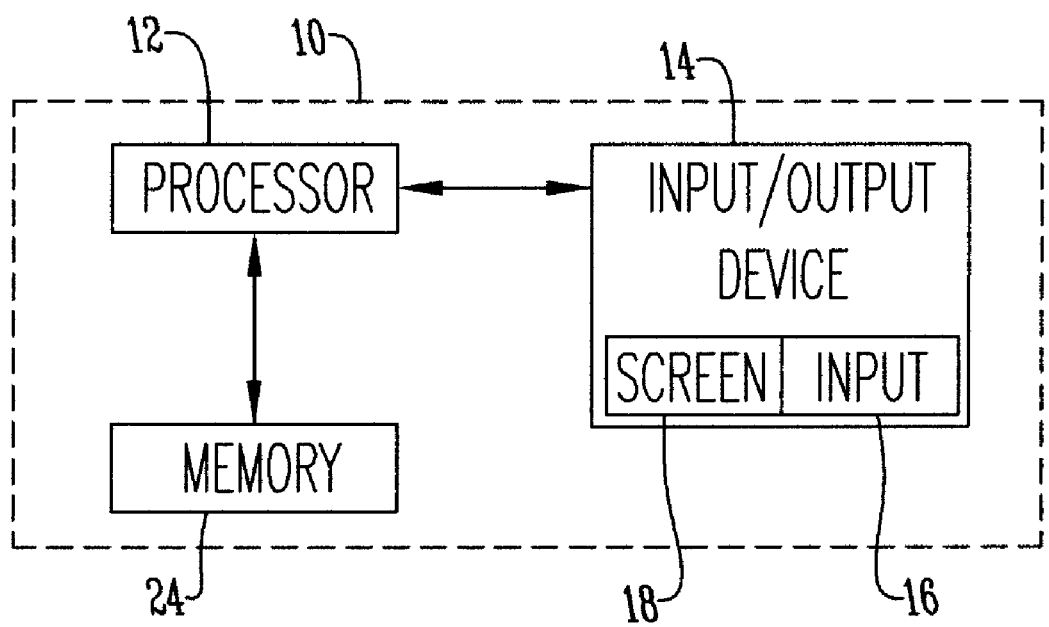
FIG. 1 is a schematic diagram of a medical device according to the present invention.

FIG. 1 is a schematic diagram of a system that has a medical device 10 therein. FIG. 1 illustrates several functional components of the medical device 10 for implementing the present invention. Those of ordinary skill in the art will appreciate that the device 10 includes many more components than those shown in FIG. 1. However, it is not necessary that all these components be shown in order to disclose an illustrative embodiment for practicing the present invention.

In the context of the present invention, the term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, a diagnostic device, or the like.

For the purpose of exemplary illustration only, the medical device 10 is disclosed as an infusion pump. More particularly, the medical device 10 can be a single channel infusion pump, a multi-channel infusion pump, or some combination thereof.

The following definitions are not intended to be limiting, but are included below to aid one skilled in the art in understanding this disclosure.

"Patient medical information" as used herein means information about a patient, including but not limited to weight, height, body surface area (BSA), known drug allergies or tolerances or permissible levels, name, or patient ID. It will be appreciated by one skilled in the programmable medical pump art from the description herein that patient medical information can be input and stored at the pump using the input device, received by the pump from a computer or storage device connected wirelessly or by hard wire to the pump, or received as part of a drug library by the pump from a computer or storage device connected wirelessly or by hard wire to the pump.

"Medication information" as used herein means information about the medication to be administered to a patient, including but not limited to drug name, drug alias, drug ID, drug trademark, drug generic name, concentration, drug amount, drug units, container volume, or dosing units.

"Pump operating parameters" as used herein means input parameters or information that affects the behavior of a pump and delivery of medication by it, including but not limited to dose, dosage, dose rate, dose amount, rate, time, volume infused or volume to be infused (VTBI).

"Pump programming parameters" as used herein broadly includes parameters that are programmed into a pump by the user or otherwise and may include one or more of pump operating parameters, medication information, patient medical information or calculations based thereon or combinations thereof. Pump programming parameters may have hard and/or soft limits applied to them through a factory or hospital customizable drug library that is resident in the device or electronically downloadable thereinto.

"Medical device capabilities" as used herein means capabilities or limitations on a pump or infuser as determined by the manufacturer's recommendations, hardware, software, administration set, primary/secondary line considerations, or other constraints. In one example, the infuser may have a minimum and/or maximum rate at which it can deliver. In another example, primary and secondary lines may have predetermined interrelated maximums so as to avoid creating any vacuum or inadvertent flow problems. By way of example only, the primary line maximum rate could be 1000 ml/hr while the secondary line rate could be limited to a maximum of 500 ml/hr.

With reference to FIG. 1 the medical device 10 includes a processor 12 that performs various operations described in greater detail below. An input/output device 14 allows the user to receive output from the medical device 10 and/or enter information into the medical device 10. Those of ordinary skill in the art will appreciate that input/output device 14 may be provided as single devices such as a separate input device 16 and an output device 18 that in one embodiment is a display device such as an output screen and in another embodiment is a voice command that states ranges or outputs. In another embodiment the input/output device 14 is a touch screen that serves both as the input device 16 and as a visual display or screen for the output device 18.

In an alternative embodiment the medical device is a medication management system (MMS) and the input/output device 14 is a drug library editor as described in U.S. Publication No. 2005/0144043 and that reference is incorporated in full in this application. In this embodiment input device 16 communicates with a MMU (Medication Management Unit) to assist in processing drug orders for delivery through the MMU. The input device 16 can be any sort of data input means, including those adapted to read machine readable indicia such as barcode labels; for example a personal digital assistant (PDA) with a barcode scanner. Alternatively, the machine readable indicia may be in other known forms, such as radio frequency identification (RFID) tag, two-dimensional bar code, ID matrix, transmitted radio ID code, human biometric data such as fingerprints, etc. and the input device 16 adapted to "read" or recognize such indicia. The input device 16 can be a separate device from the medical device 10; alternatively, the input device 16 communicates directly with the medical device 10 or may be integrated wholly or in part with the medical device.

A memory 24 communicates with the processor 12 and stores code and data necessary for the processor 12 to perform the functions of the medical device 10. More specifically, the memory 24 stores multiple programs and processes formed in accordance with the present invention for various functions of the medical device 10.

Referring to FIGS. 2-12 various screen shots of the input/output device 14 are displayed to a user of a medical device 10. As described herein, the input/output device 14 is in the context of an infusion pump; however, this is for exemplary purposes only. Other instruments may incorporate aspects of the invention and generate audio output or present a graphic display to communicate data.

Figure 3:
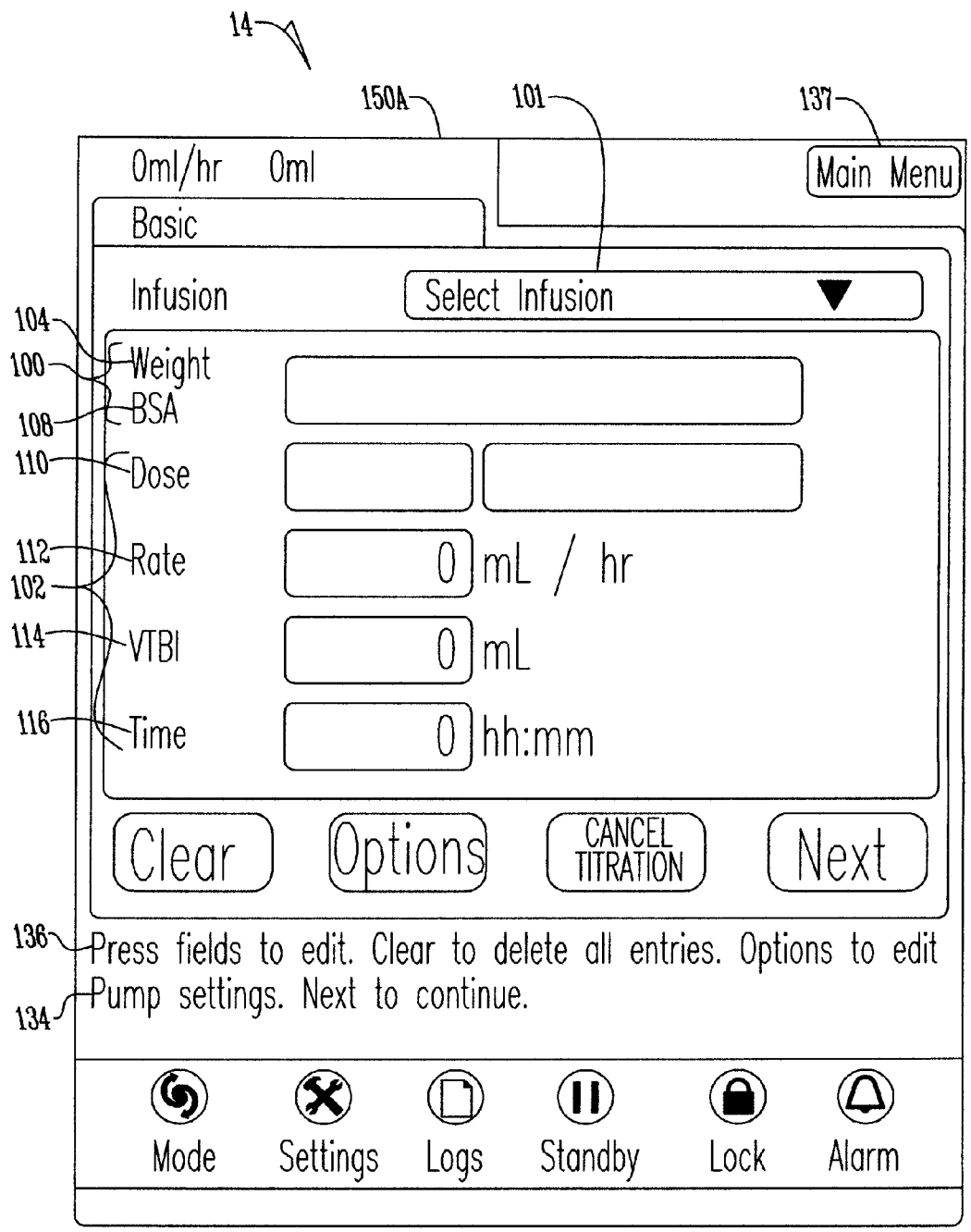
FIG. 3 is a screen shot of a near view programming screen that can be used to initially program a basic therapy according to the present invention.
Figure 6:
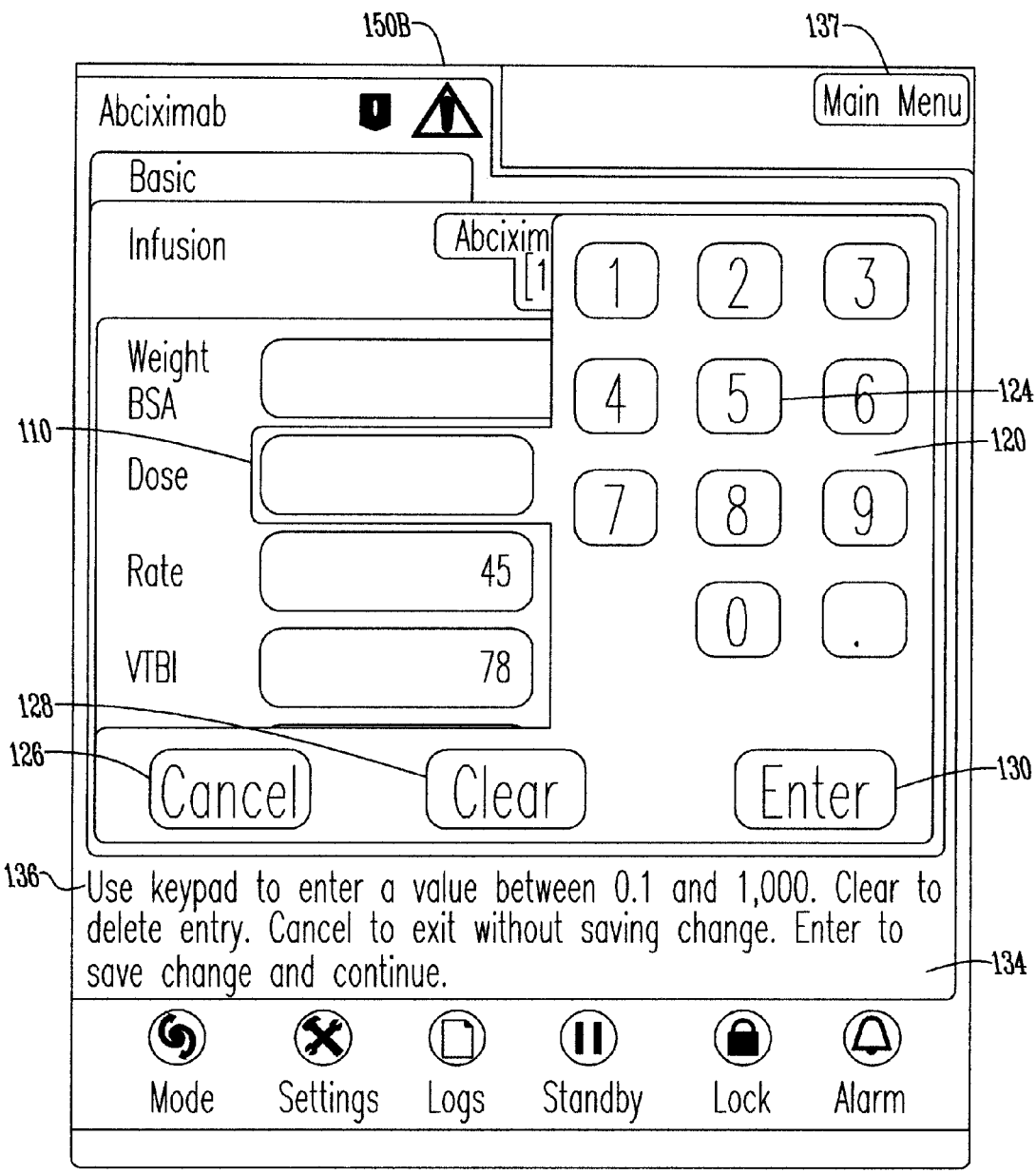
FIG. 6 is a screen shot showing a near view programming or titration screen that is displayed when one the quick titration buttons on the far view delivery screen of FIG. 5 is selected or pressed.
Figure 7:
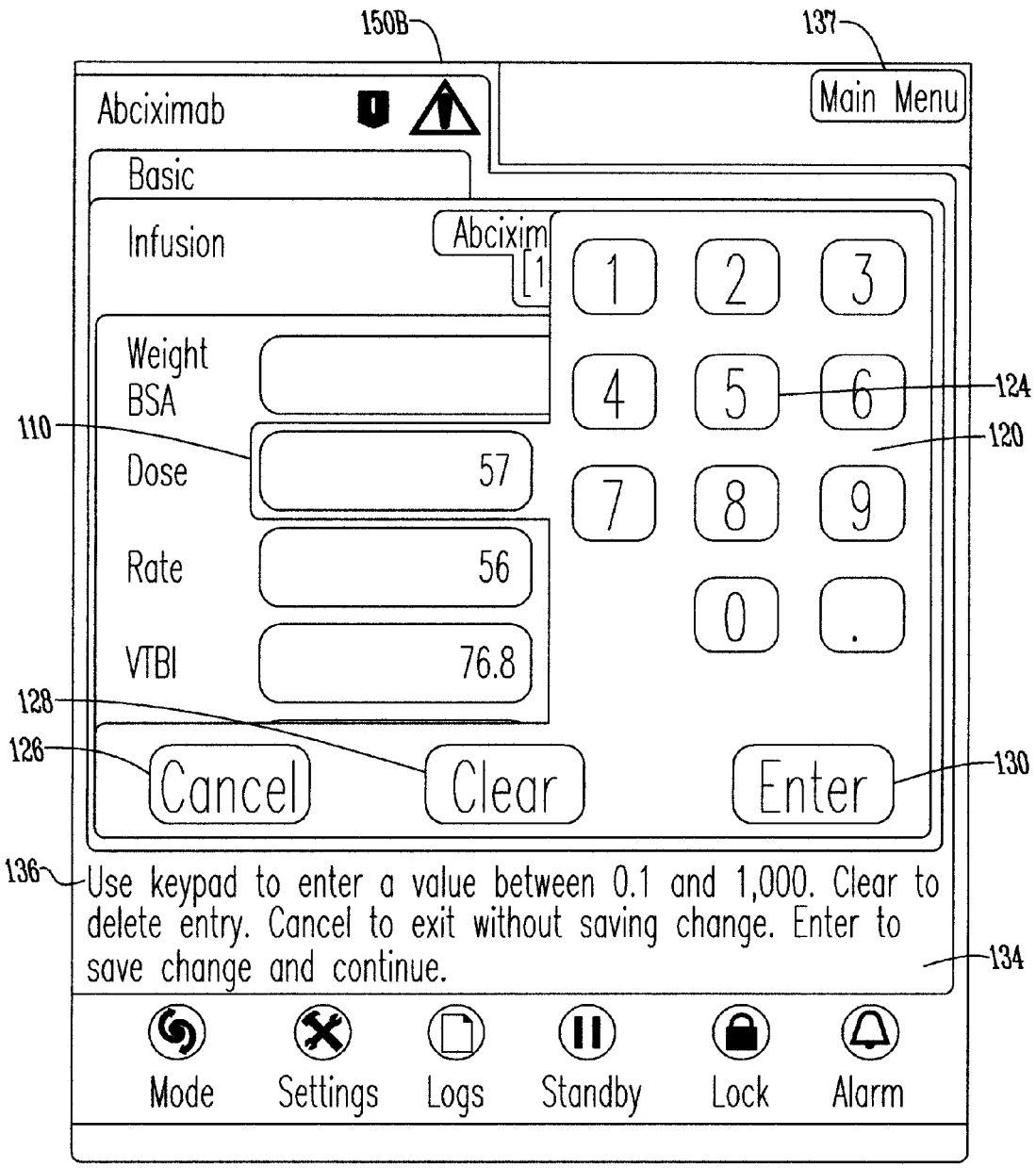
FIG. 7 is a screen shot showing a near view programming screen that is displayed after a numerical value has been selected for input using the keypad.
Figure 8:
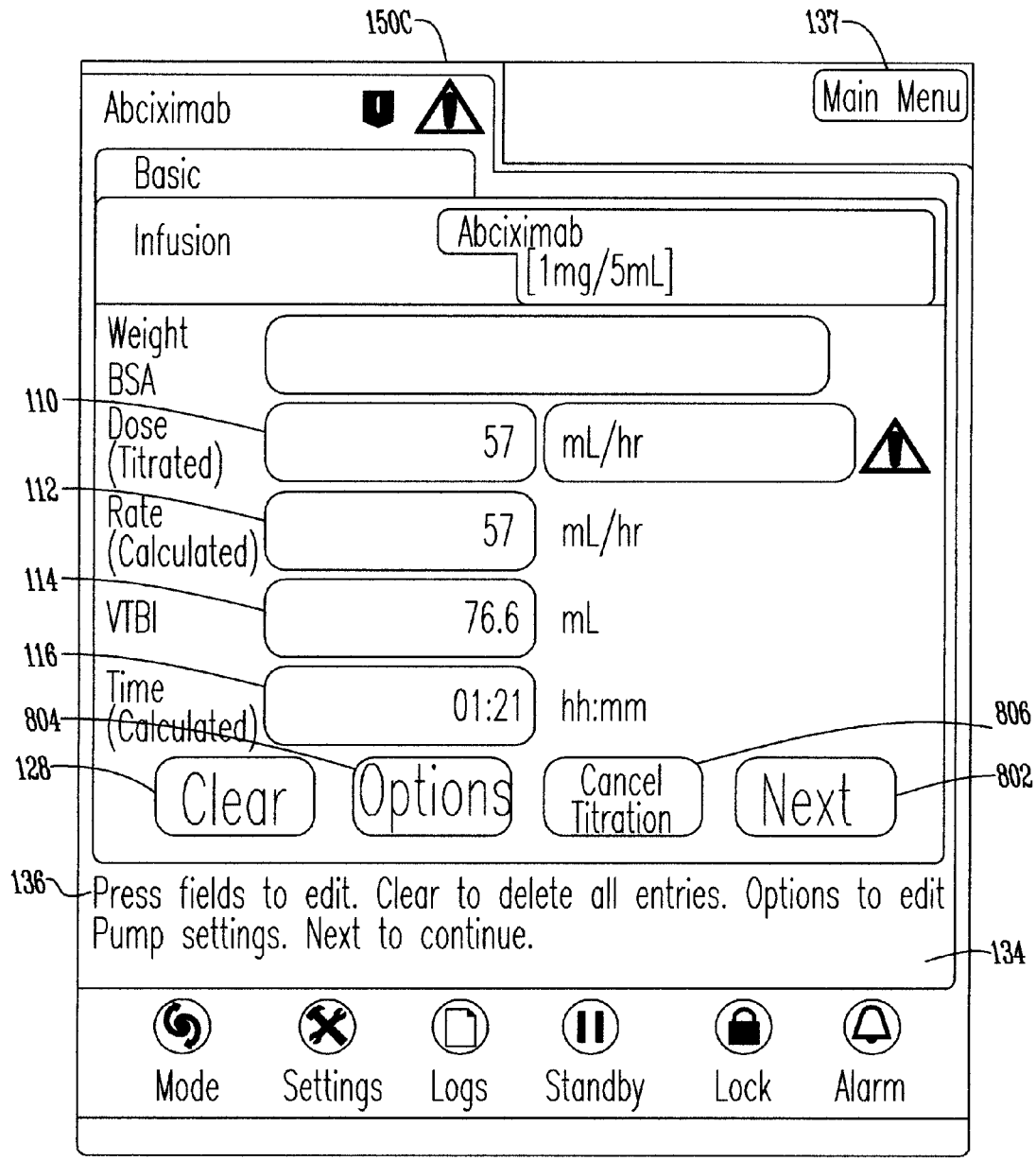
FIG. 8 is a screen shot showing a near view programming screen that is displayed when the Enter button on FIG. 7 is selected or pressed.

As best shown in FIG. 3, the input/output device 14 as part of its input device functionality provides a near view initial programming screen 150A with several entry points or fields wherein patient medical information 100, medication information 101 and pump programming parameters 102 may be entered. Specifically, patient medical information 100 such as a patient's weight 104, height (not shown) or BSA (body surface area) 108 may be entered. Medication information such as the name and concentration of a medication may be entered or selected from a drop down menu based upon a predetermined user customized drug library. Additionally, as illustrated in FIGS. 3 and 6, pump operating parameters 102 such as dose 110, rate 112, volume (infused or VTBI (volume to be infused)) 114, time 116 and dose amount (not shown) may be entered using a numerical key pad 120 that pops up when a particular field is touched and allows input of numerals 124 on the key pad 120. The key pad 120 additionally has a CANCEL button 126 if a user desires to exit and return to the previous screen without saving or entering information, a CLEAR button 128 to clear an input and an ENTER button 130 to enter an input. Thus, a numerical value can be given using the key pad 120 to provide a numerical value for the height, weight or BSA of the patient or the dose rate, dose amount, rate, volume infused or VTBI, or time or duration of the infusion.

Additionally, on the input/output device 14 as part of its output device functionality displays a text box 134 wherein a message 136 can be provided to the user regarding the data to be entered or the entered data provided. Specifically, the text box 134 can provide whether the entered pump programming parameters are proper. The text box 134 can also provide the user advance guidance on the valid range of values that can be entered, or whether a valid range exists.

The message 136 provided depends upon the data entered or to be entered into the medical device 10. For example, the message can indicate that an invalid program parameter combination is entered. This indicates to a user that for the parameters selected there is no valid range that can be calculated. Alternatively, if a valid range exists, this valid range is displayed. Whereas if the data point entered is invalid the message 136 indicates an invalid value has been entered.

A MAIN MENU button 137 is presented or displayed on the near view screens 150-150E. When a user touches this button the processor 12 causes the input/output device 14 to display or return to the main menu far view screens of FIG. 4 or 5. If the pump is already programmed and/or executing an infusion or fluid delivery program when the user touches the MAIN MENU button 137, the processor will return the user to the far view screen of FIG. 5. If the pump is idle or not yet programmed, the processor 12 will display the far view screen of FIG. 4 when the user touches the MAIN MENU button 137.

Figure 2:
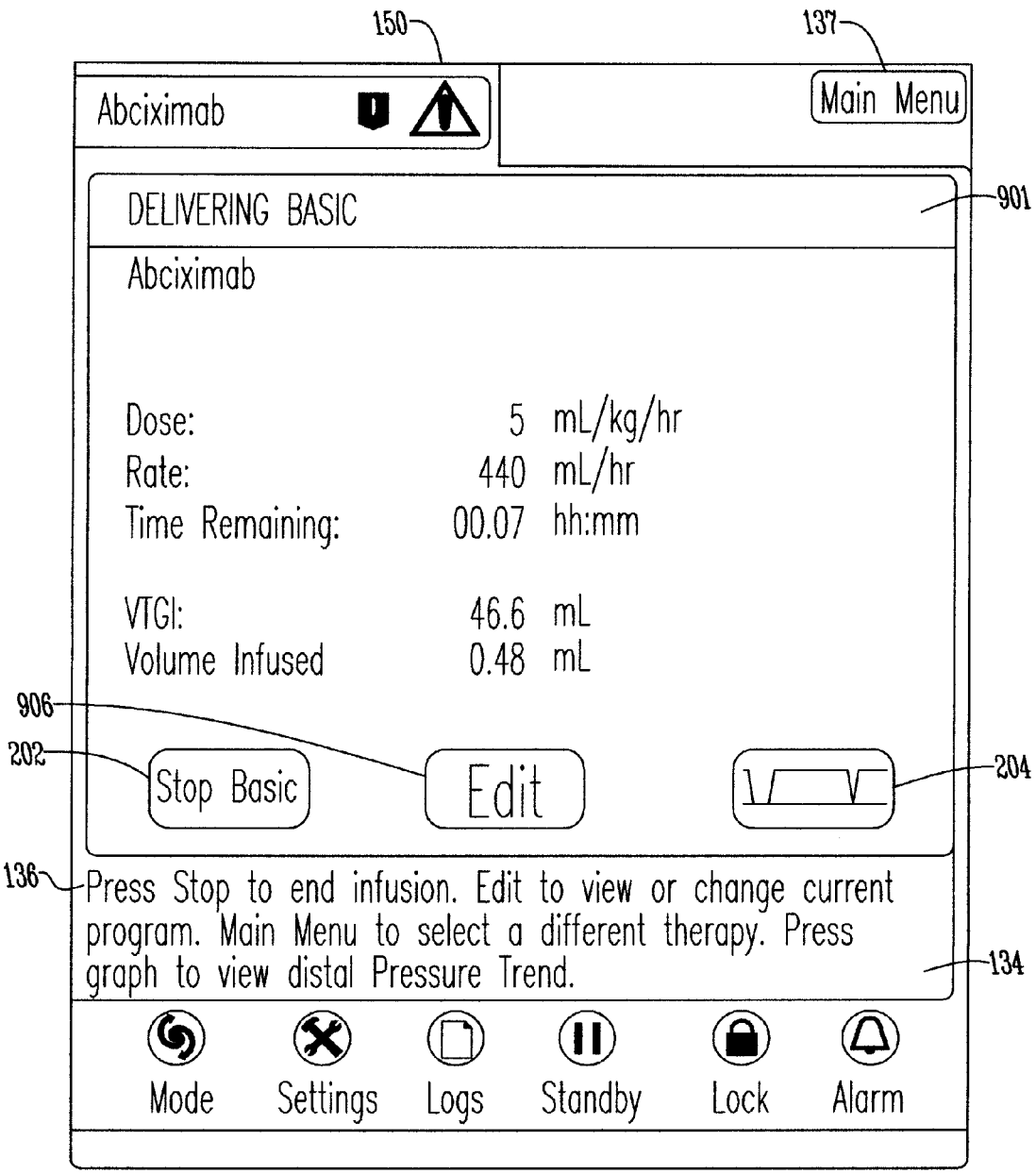
FIG. 2 is a screen shot of a near view delivery screen of a medical device according to the present invention.
Figure 4:
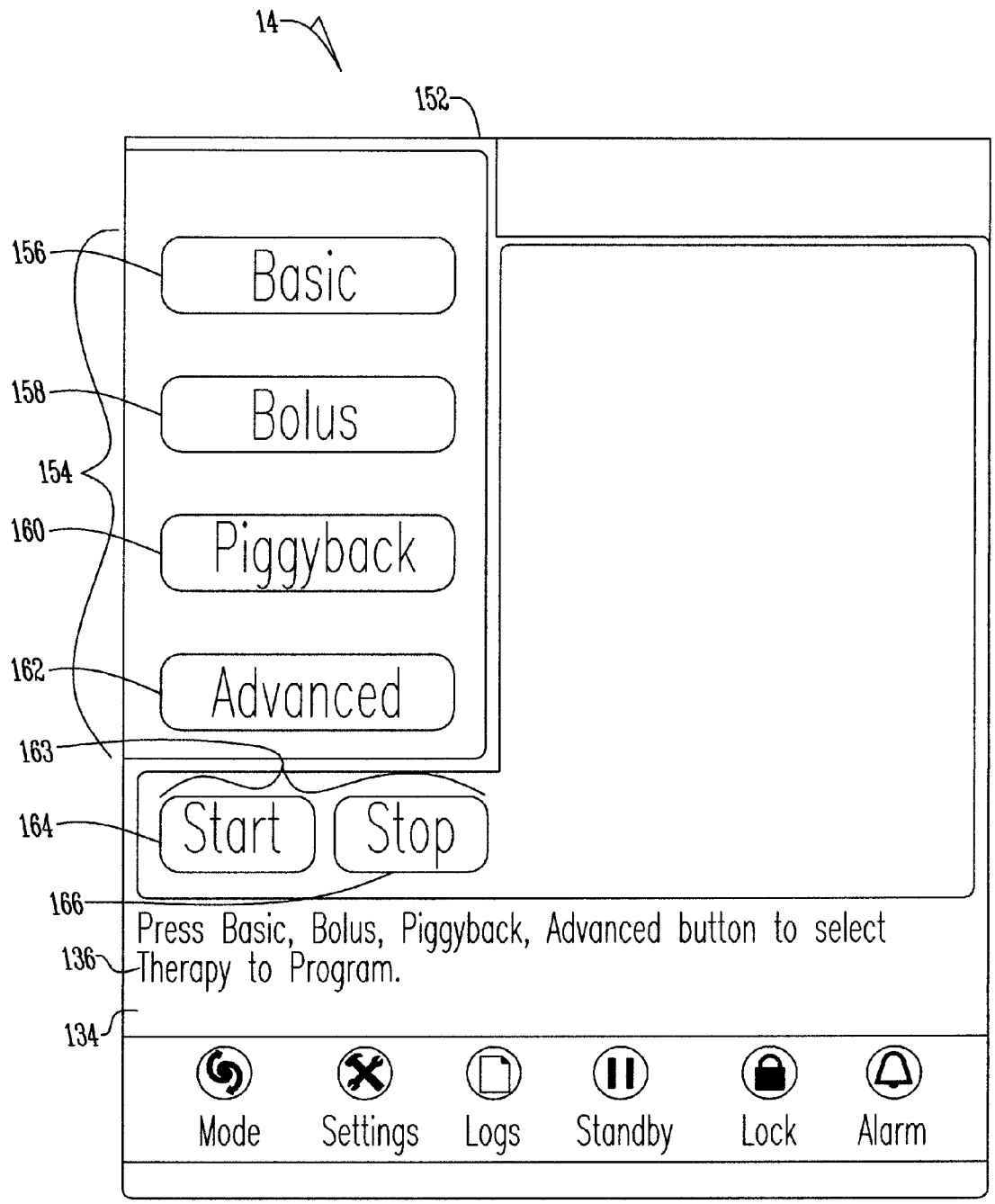
FIG. 4 is a screen shot of a far view screen in a first (idle or unprogrammed) condition of a medical device according to the present invention.
Figure 5:
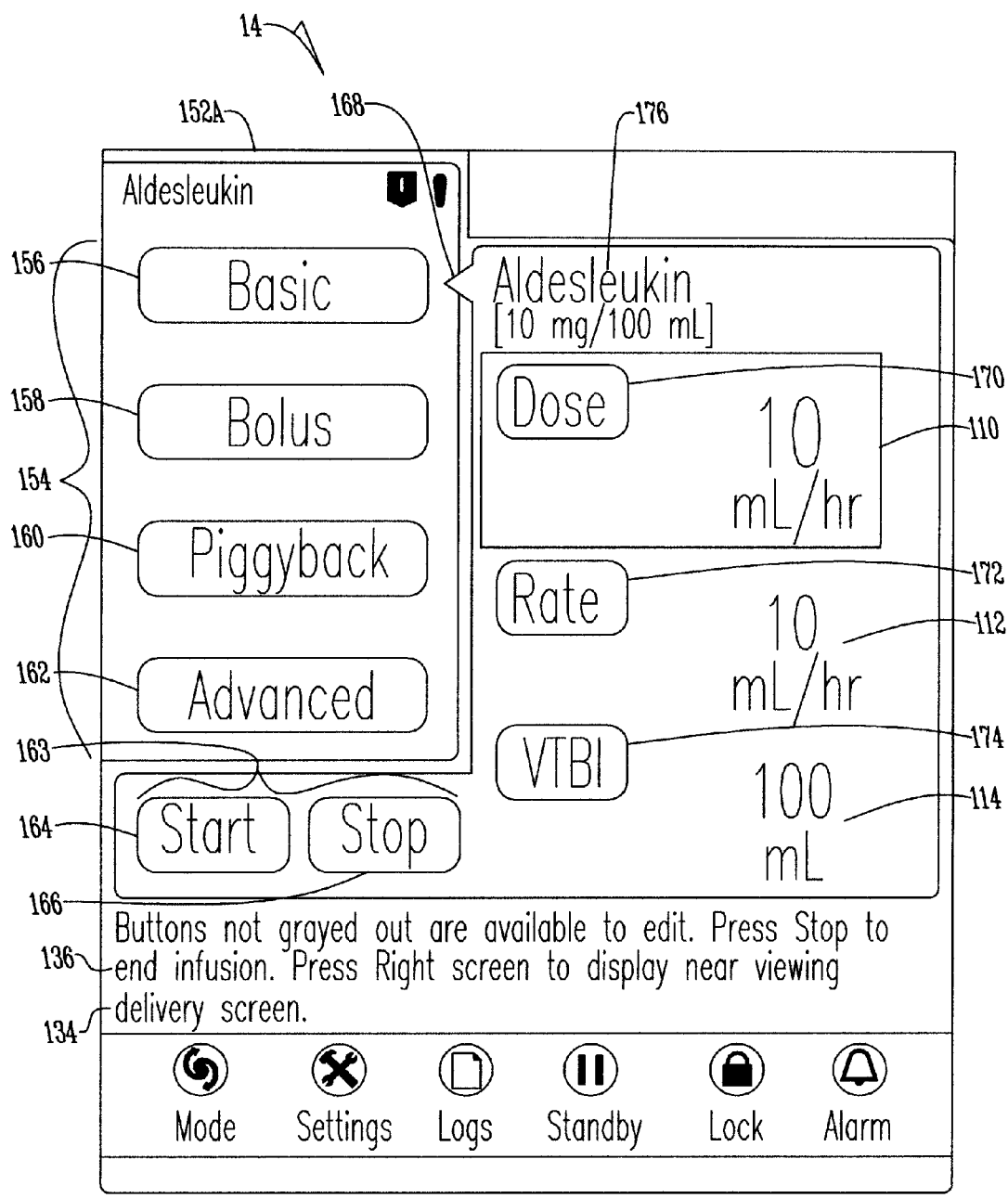
FIG. 5 is a screen shot a far view delivery screen in a second (programmed and/or delivering) condition of a medical device.

FIGS. 2 and 3 show screen shots on the input/output device 14 that are considered near view screens 150, 150A. As discussed in the Background the near view screen allows viewing and entry of a full compliment of medical data and is generally used to access more detailed information or programming screens to program the medical device 10. Medical data including patient medical information 100, medication information 101, and pump programming parameters 102 are entered and displayed on the near view screens 150. FIGS. 4 and 5 meanwhile represent far view screens 152, 152A, each of which may constitute a default or main menu screen. Specifically for example, the processor 12 of the medical device 10 can be factory set or programmed or configured by a user, biomedical engineer, pharmacist or other hospital personnel such that when a predetermined amount of time passes and information has not been entered into the near view screen 150 the near view screen 150 times out in order to display the far view screen 152 for better viewing from across a room and/or to reduce power consumption by allowing backlighting of the touch screen input/output device 14 to be reduced when an individual is not actively programming the device. Referring to FIG. 2, a STOP BASIC button 202 is displayed on the near view delivery screen 150. The STOP BASIC button 202 terminates the basic therapy when the button is pressed by the user.

As best shown in FIGS. 4 and 5 the far view screen 152, 152A of the present invention presents a plurality of medical therapy buttons 154 including but not limited to a BASIC button 156, a BOLUS button 158, a PIGGYBACK button 160, and an ADVANCED button 162. The therapy buttons 154 are arranged on a common widget on one portion of the screen, for example a side, in order of most frequent use for a general purpose infusion pump. In one embodiment, the buttons 154 are arranged BASIC button 156, BOLUS button 158, PIGGYBACK button 160, and then ADVANCED button 162 from top to bottom. Since their placement on the screen 152, 152A is software driven, the therapy buttons 154 could be arranged in other ways, including but not limited to alphabetically by initial letter, left to right for left to right language reading countries, right to left for right to left language reading countries. All of this could be set in a fixed manner by the manufacturer or made configurable or user customizable via one or more settings in the pump or in a drug library downloaded to the pump.

The far view screen 152, 152A also presents therapy start/stop buttons 163 that include a START button 164 and a STOP button 166 to start or halt a therapy respectively. Although they could be presented or displayed on the same widget as the therapy buttons 154, in the exemplary embodiment shown the start/stop buttons 163 are displayed or presented concurrently on a separate widget on a portion of the screen 152, 152A adjacent to the therapy buttons 154. In one embodiment the processor 12 displays the start/stop buttons 163 on a portion of the screen directly below the therapy buttons 154. Presenting the START button 164 and the STOP button 166 together, adjacent to, or in close proximity to each other on the same far view screen 152, 152A saves the user time when starting or stopping the therapy. Previously, displayed start and stop buttons appeared on different screens that required additional touches to navigate between. An emergency stop button was also previously provided remote from the display screen of the input/output device 14, but activating it caused other undesirable emergency responses from the pump, including an audible and/or visual nurse call alarm in addition to merely stopping the therapy. These other responses could disturb a resting patient or annoy a caregiver trying to stop or pause therapy. In the present invention, when the user touches the STOP button 166, a status/suggestion banner similar to 901 (FIG. 9) is displayed on the screen with a message like "STOPPED BASIC", but no audible alarm is generated and the user is not presented with or transitioned to a new screen. The START button 164 is thus immediately available to restart the therapy from the same screen if desired.

In addition, in one embodiment illustrated in FIG. 5, when the pump is delivering or operational and the user touches the BASIC button 156, the far view screen 152A can concurrently provide or display current pump operating information for the therapy such as dose 110, rate 112 and volume (infused or volume to be infused (VTBI)) 114 information for a viewer. In the embodiment shown, the current pump operating information is displayed on the same widget as the stop/start buttons 163 and in a side by side relationship with the therapy buttons 154. A pointer 168 is optionally provided to point to the particular therapy button 156, 158, 160, or 162 to which the displayed current pump operating information applies or is associated with.

In operation, as shown in FIGS. 4 and 5, the processor 12 presents a far view or main menu screen 152, 152A most of the time, unless the user is actively programming the pump.

The programming code of the processor 12 is operable to display a far view screen 152, 152A that has a plurality of medical therapy buttons 154. In one embodiment, when the user touches or presses one of the medical therapy buttons 154, such as 156, 158, 160 or 162, the programming code causes the processor 12 to display the corresponding current pump operating information for that therapy on the same screen. Quick titration buttons 170 for DOSE, 172 for RATE and 174 for VOLUME (infused) or VTBI are presented as part of or adjacent to the corresponding operating information. Thus, while viewing the current operating information, the clinician is able to complete the steps of choosing a therapy and a titration parameter to adjust or program without having to go to a different screen. When touched, the quick titration buttons 170, 172, 174 navigate the clinician directly to a near view titration screen 150B such as shown in FIG. 6. Specifically, when a button such as the BASIC button 156 is touched a clinician may directly input medical information without the need to go through a general near view delivery screen 150, a menu or be presented with a vastly different appearing screen because the near view titration screen 150B is navigated to directly from the far view delivery screen 152A.

In another embodiment, when the user touches or presses one of the medical therapy buttons 154 on FIG. 4 or FIG. 5, such as 156, 158, 160 or 162, the programming code causes the processor 12 to immediately display a near view programming screen. For example, when the user presses the BASIC therapy button 156, the basic therapy programming near view screen 150A of FIG. 3 is displayed. If the user touches one of the other therapy buttons, another near view programming screen appropriate for that therapy is displayed. For example, when the user touches the ADVANCED therapy button 162, an advanced therapy near view programming screen is displayed. Alternatively, if the pump is in a delivering or programmed condition and the far view delivery screen 152A of FIG. 5 is displayed, the user can instead select or press one of the quick titration buttons 170, 172, 174 to immediately navigate directly to a near view titration screen such as 150B of FIG. 6.

As best understood in view of FIGS. 3-9, once the clinician selects a particular parameter to program or adjust and is presented with the near view titration screen 150B and the numerical key pad 120 shown in FIG. 6, they can enter a desired numeric value for the particular pump operating parameter selected. In the example illustrated by FIG. 7, the user has touched the appropriate numeral keys 124 on the key pad 120 to type the numeral "57" in the field for dose 110. When the clinician presses the ENTER button 130 in FIG. 7, the processor 12 saves or enters the numerical value and recalculates any related parameters as shown in the near view screen 150C of FIG. 8. The processor 12 displays the near view confirmation screen 150D of FIG. 9 when the user presses the NEXT button 802 in FIG. 8 to continue. Otherwise the clinician can press other fields 112, 114, 166, etc. to edit those parameters, delete all entries with the CLEAR button 128, press the OPTIONS button 804 to edit pump settings like alarm thresholds for air-in-line, distal occlusion pressure, proximal occlusion pressure, and nearing end of infusion or priming rate, KVO rate, and end of infusion alarm, or cancel the titration with the CANCEL TITRATION button 806.

Figure 9:
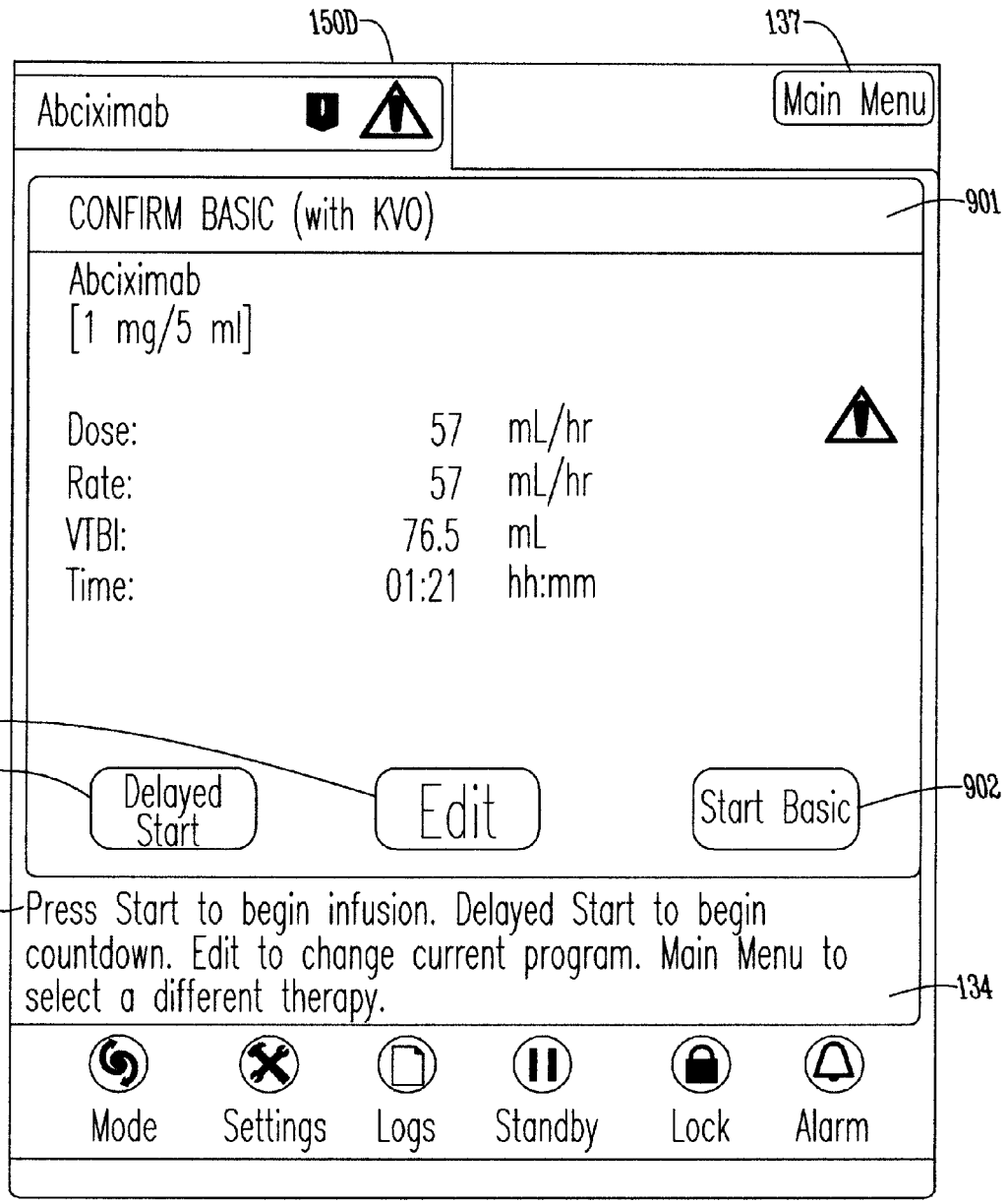
FIG. 9 is a screen shot showing a near view confirmation screen that is displayed when the Next button on FIG. 8 is selected or pressed.
Figure 10:
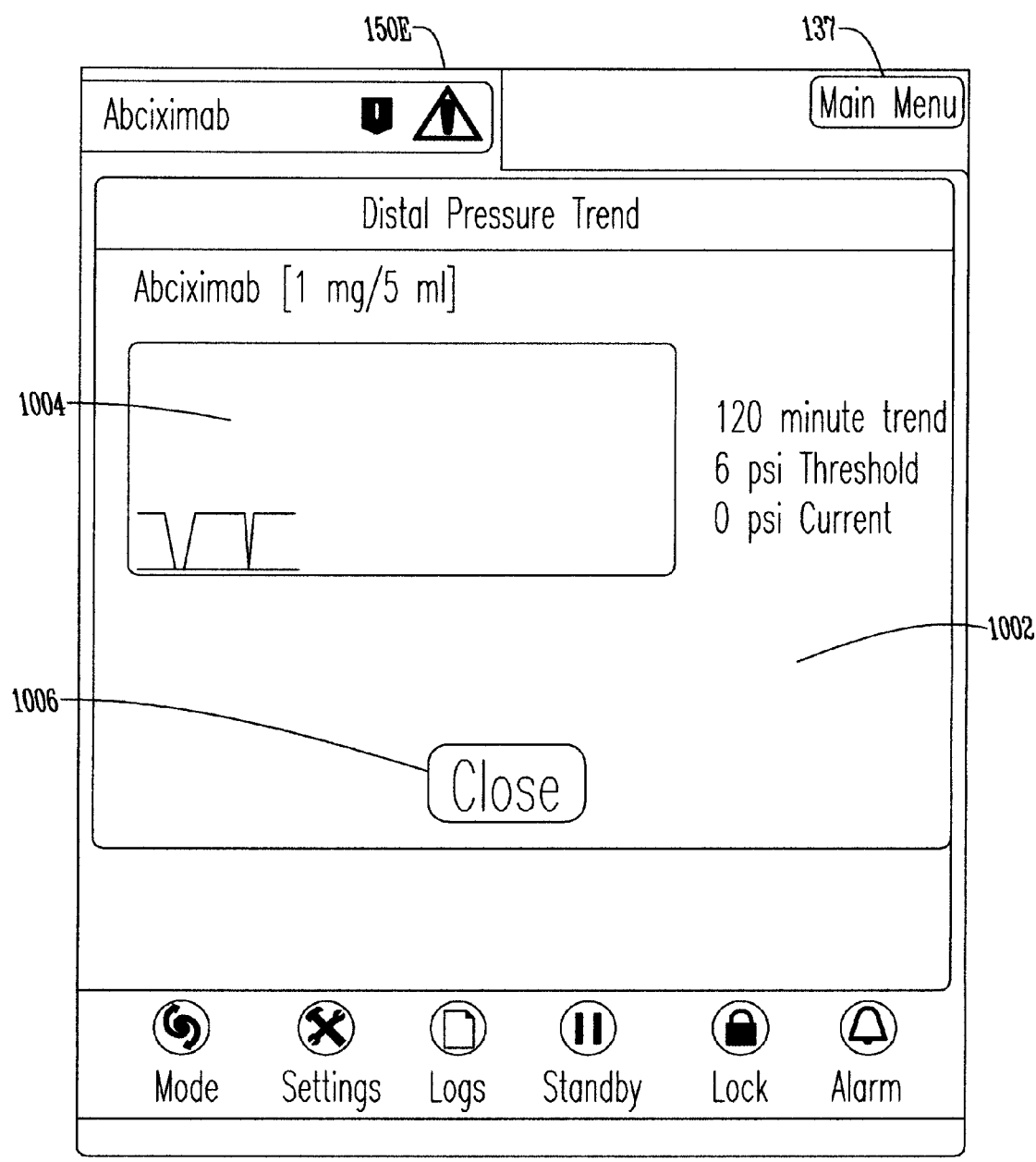
FIG. 10 is a screen shot showing a large scale graph of a distal pressure trend displayed by a pump according to the present invention.

The processor 12 displays a status/suggestion banner 901 near the top of the near view confirmation screen 150D of FIG. 9 to remind the clinician of an action that is suggested or advise them of a status of the pump. After reviewing the programming information on the near view confirmation screen 150D of FIG. 9 as suggested by the banner 901, if the parameters are acceptable, the user typically presses a start button such as the START BASIC button 902 to immediately start the infusion as programmed. Otherwise, the clinician can press a DELAYED START button 904 to start a countdown timer to delay the start of the infusion by a predetermined or configurable amount of time. The user can also touch an EDIT button 906 to return directly to the screen of FIG. 3 for basic therapy for example (other therapies have similar detailed near view programming screens). Alternatively it is contemplated that the EDIT button 906 could be programmed to take the user to one of FIG. 4 or FIG. 5 to view and change the current therapy and/or program if desired. The EDIT button 906 is a new addition to the near view screens and provides an improvement over the previous more indirect circular, linear or serial progression form of navigation between the confirmation screen and the programming screen of FIG. 3. The clinician can also touch the MAIN MENU button 137 to return to the screen of FIG. 4 or 5 to select a different therapy and/or parameter and begin the programming or program modification process all over again.

Another aspect of the present invention is a graphical distal pressure button 204, which in the embodiment shown is displayed to the user on the near view delivery screen 150 but could be displayed on other near view or far view screens. The distal pressure button 204 includes on the button itself a relatively small scale, abbreviated time versus pressure graph of the most recent actual history of distal pressure recorded by the pump 10 over a first predetermined short period of time. By way of example and not limitation, the time period can be factory determined or user customizable via pump settings or a drug library to be 10, 20, 30 or 60 seconds. The distal pressure button 204 serves multiple functions. It intuitively provides the user with an indication of the type of data that is accessible by the button, while displaying a recent history or snapshot of the data in question, which allows the user to monitor for any problems with the data and delve deeper if needed. The clinician can touch the distal pressure button 204 in FIG. 9, especially if they view a possible abnormality on the abbreviated graph, and the processor 12 will display a distal pressure screen 1002 such as shown on the screen 150E in FIG. 10. The distal pressure screen 1002 includes a graph 1004 of distal pressure that is larger than the graph on the button 204 and graphically depicts distal pressure over a second greater period of time so as to provide a larger, longer graph of distal pressure trend. Similar to the graph on the button 204, the time period for the distal pressure trend graph 1004 shown in FIG. 10 can be factory determined or user customizable via pump settings or a drug library. By way of example and not limitation, the time period for the larger, more detailed trend graph can be 5, 10, 30, 60, 90 or 120 minutes.

On both the thumbnail graph on the distal pressure button 204 and the larger distal pressure graph 1004 on the trend display 1002, color coding can be provided to show an alarm threshold pressure in a first color, such as red, for example, and the current pressure in a different or second color, such as blue, for example. Further legends, keys and labeling can also be provided, especially on the larger trend display 1002. On the screen 150E of FIG. 10, a CLOSE button 1006 is displayed for the clinician to touch to return to the near view delivery screen 150 of FIG. 2. Optionally, a MAIN MENU button 137 is displayed and can be made active or available for the clinician to touch to return to the far view delivery screen 152A of FIG. 5. The trend display concept described above can be applied to the display of other information on the pump, including but not limited to patient vital signs (heart rate, blood pressure, respiration rate, $CO_2$, $SpO_2$, temperature, etc.), lab values (glucose, aPTT, etc.), and other pump operating information (air-in-line, temperature, noise, vibration, battery energy used or remaining, etc.).

Figure 11:
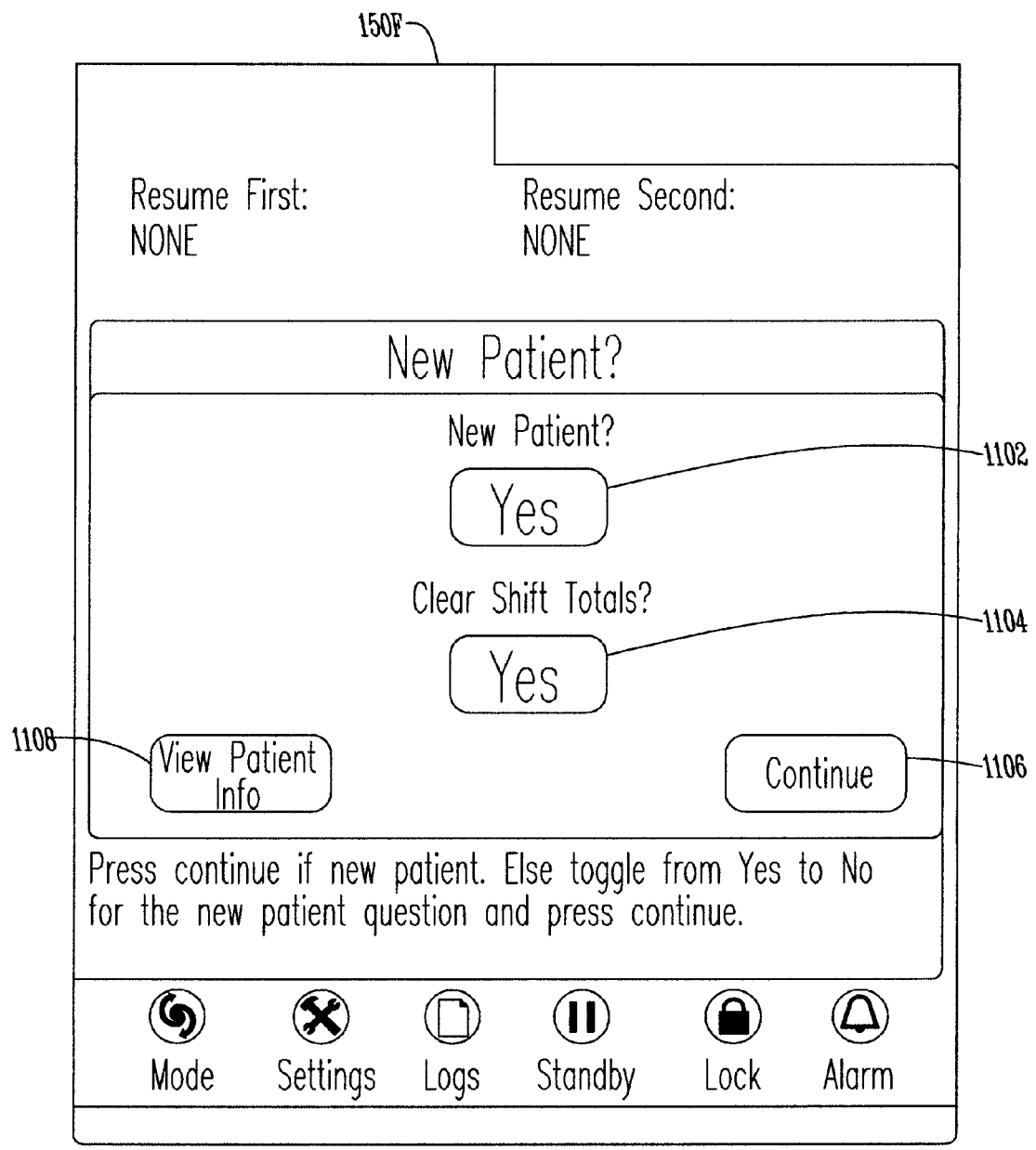
FIG. 11 is a screen shot showing a new patient screen of the present invention in a first condition.
Figure 12:
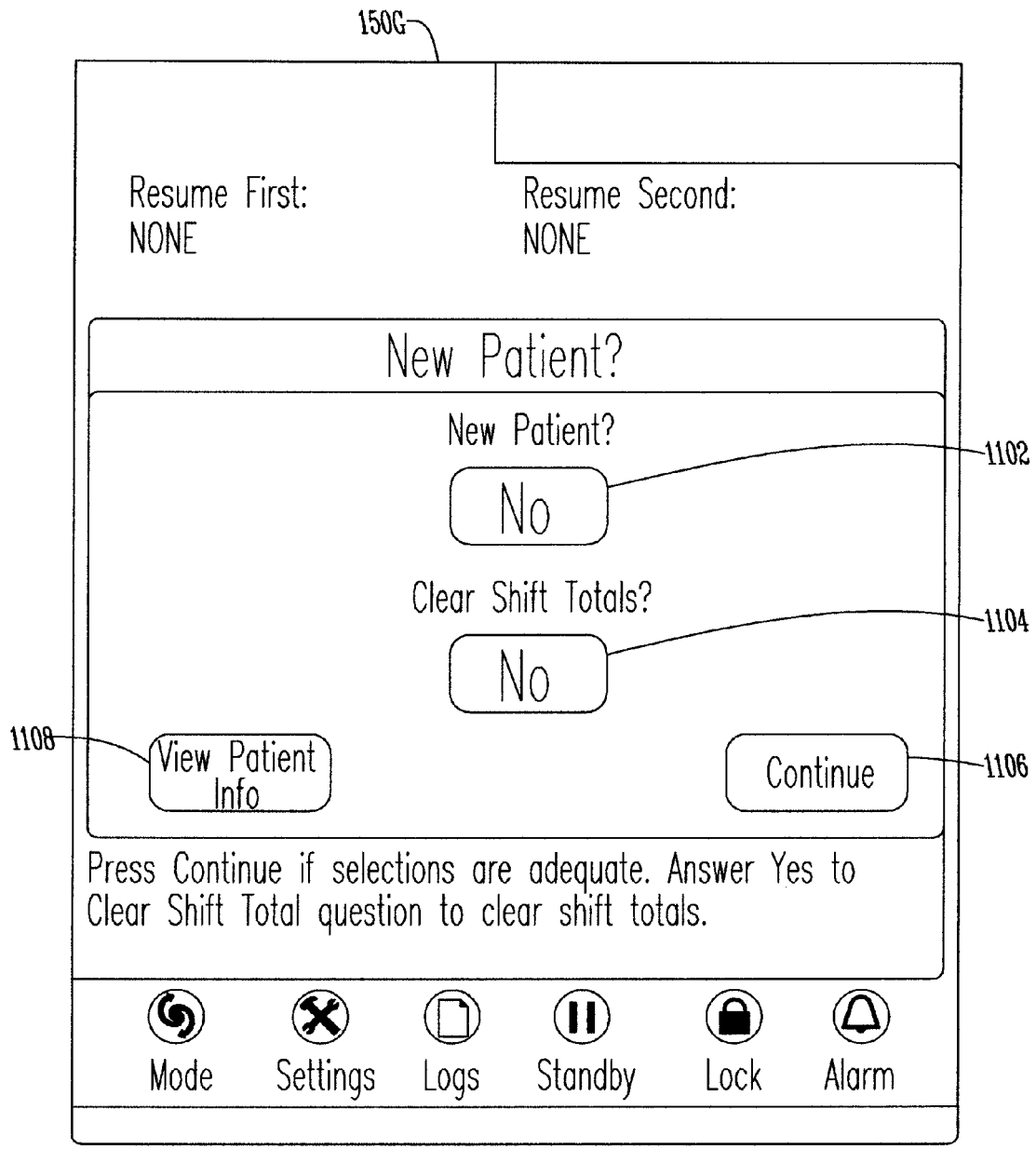
FIG. 12 is a screen shot showing the new patient screen of the present invention in a second condition.

With reference to FIGS. 11 and 12, the invention provides an improved new patient near view screen 150F, 150G that includes NEW PATIENT and CLEAR SHIFT TOTALS buttons 1102 and 1104 respectively that maintain a fixed position on the screen 150 but toggle their text and corresponding function/response when touched by a user to display one selection from a plurality of different selections. In the example shown, the selection can be YES or NO. When a button 1102 or 1104 displaying the selection YES is touched by the user, the selection displayed is changed by the processor 12 to NO, and vice versa. To lock in and enter the displayed selection, the user presses a CONTINUE button 1106 on the touch screen. A VIEW PATIENT INFO button 1108 is displayed to allow the user to check or view the information the patient information the pump currently has stored. Each of the toggling buttons 1102 and 1104 takes far less space and time than a drop-down menu or list that must be scrolled through. Thus, the button can be enlarged for easier viewing and more reliable activation. The processor can also be programmed or configured to show the most likely selection based on pump or therapy status. For example, if the pump has not reached the end of a therapy or has not been shut off for a predetermined period of time, the NEW PATIENT button 1102 might be configured to display the selection NO, whereas if the pump has been powered off or the therapy ended more than a predetermined period of time ago the button 1102 might display YES.

Figure 13:
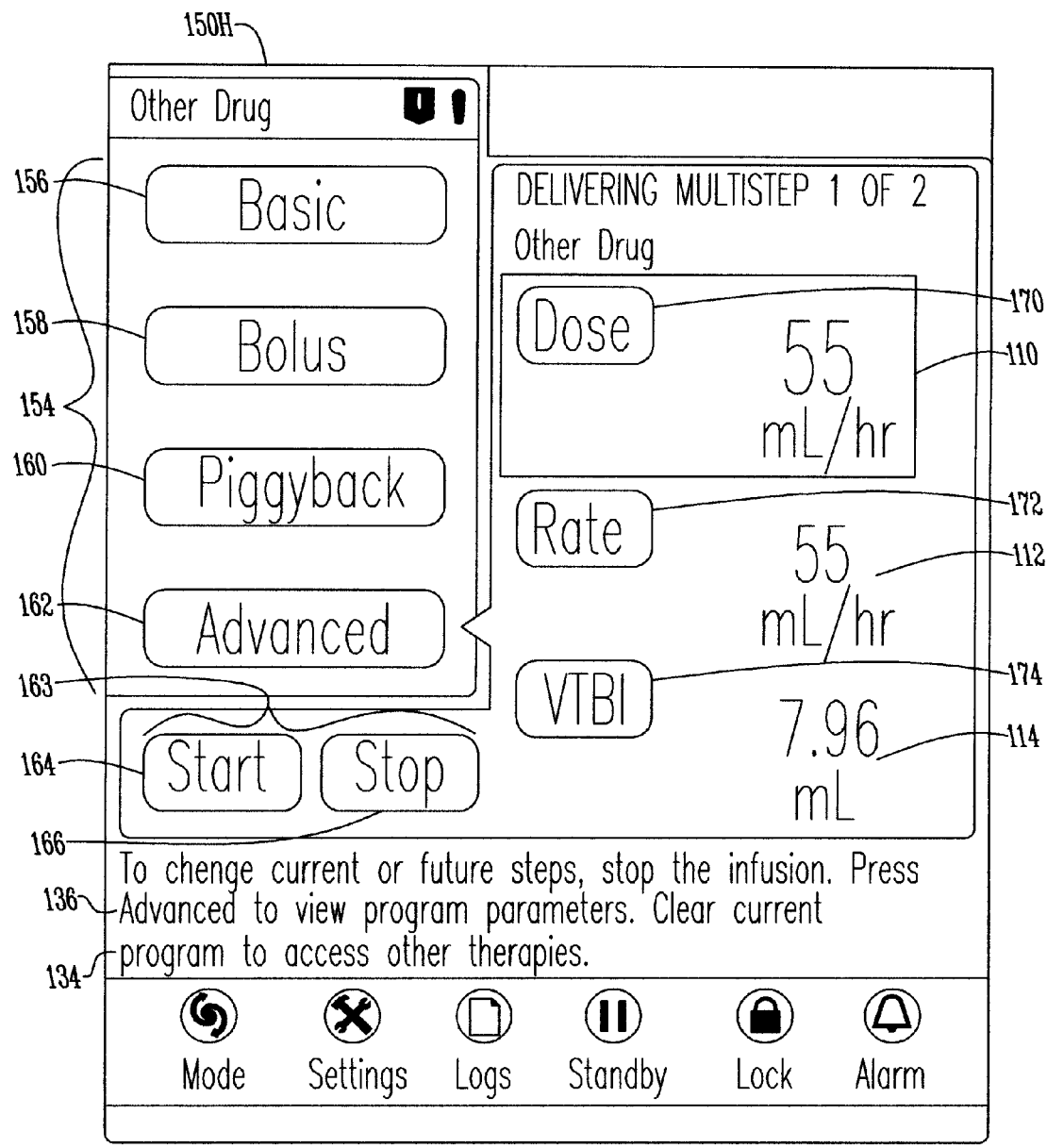
FIG. 13 is a screen shot similar to FIG. 5 but shows a far view screen that displays information about an advanced infusion.

Referring to FIG. 13, a far view screen 150H is displayed that provides information about an advanced infusion. In the illustrated example, the advanced infusion is a multistep infusion, more particularly a two step infusion. The nature and status of the advanced infusion is advantageously indicated for the user on the far view screen by a status message 901, which saves the user the step of going to other screens to find this information.

As will be understood by one skilled in the art from the description above, the present invention provides a number of timesaving improvements related to using and programming a medical device such as an infusion pump. By having the plurality of medical therapy buttons 154 and the quick titration buttons 170, 172, 174 on the far view screen 152A a clinician may quickly access a near view titration screen 150B by pressing one of the plurality of medical therapy buttons 154 and the desired quick titration button 170, 172, 174 in order to immediately start inputting information without additional button pressing, going through multiple other screens, buttons, tabs, menu items or the like. Each time a completely new screen is presented to the user, the user must cognitively process and peruse it briefly to understand the information presented. This process is mentally taxing and takes time for the user to complete. Thus, the pop-ups and combination of buttons of the present invention that appear on the same screen, are quicker to use than drilling through a series of different screens. Thus, a clinician may efficiently program the pump 10 minimizing the amount of screens that need to be accessed and buttons 154 that need to be pressed in order to input data into the pump. Consequently, at the very least all of the stated objectives have been met.

It will be appreciated by those skilled in the art that other various modifications could be made to the device without departing from the scope of this invention. For example, it is contemplated that the overlays or the pop-up keypad 120 and other features of FIGS. 6 and 7 could incorporated into the far view screen of FIG. 5 so that even more programming steps could be completed without leaving the far view screen. All such modifications and changes fall within the scope of the claims and are intended to be covered thereby.

What is claimed is:

1. A medical pump system comprising:
an input device for entering one of a command and a value of a pump programming parameter;
a memory for storing programming code;
a processor in communication with the memory and the input device being operable to execute the programming code and, in response to at least one of the programming code, the command, and the value of the pump programming parameter, generate a display signal;
an output device in communication with the processor to receive the display signal and in response to the display signal generate one of a plurality of screens, the plurality of screens including a far view screen and a near view screen;
wherein the programming code is operable to display on the far view screen a plurality of medical therapy buttons, at least one of the medical therapy buttons, when activated by a user, displaying one of a near view programming screen and a plurality of quick titration buttons;
wherein the programming code is operable to display the plurality of quick titration buttons on the far view screen concurrently with the medical therapy buttons; and
wherein the plurality of medical therapy buttons displayed on the far view screen include a PIGGYBACK button, a BASIC button, a BOLUS button, and an ADVANCED button.

2. The medical pump system of claim 1 wherein the programming code is operable to navigate directly to and display a near view titration screen when one of the quick titration buttons is activated by the user.

3. The medical pump system of claim 1 wherein the far view screen also concurrently displays current pump operating information selected from a group consisting of dose, volume and rate information.

4. The medical pump system of claim 1 wherein the far view screen concurrently displays a START button and a STOP button.

5. The medical pump system of claim 1 wherein the near view screen displays an EDIT button that, when activated by the user, causes the near view programming screen to be displayed.

6. The medical pump system of claim 1 wherein the near view screen displays a MAIN MENU button that, when activated by the user, causes the far view screen to be displayed next.

7. The medical pump system of claim 6 wherein the MAIN MENU button also causes the plurality of quick titration buttons to be displayed on the far view screen.

8. The medical pump system of claim 1 wherein the memory stores constraints related to the pump programming parameter and the processor is operable to determine whether a valid input range for the pump programming parameter exists and generate a display signal to the output device to display a message to the user regarding the existence of valid input range for a pump programming parameter.

9. The medical pump system of claim 1, wherein the programming code is operable to display a near view programming screen for input of pump programming parameters in response to the user touching one of the medical therapy buttons on the far view screen.

10. The medical pump system of claim 1, wherein, if the medical pump is programmed for a fluid delivery, the programming code is operable to display concurrently with the display of the plurality of user touch selectable medical therapy buttons a display of a plurality of user touch selectable quick titration buttons on the far view screen.

11. The medical pump system of claim 10 wherein, in response to the user selectively touching one of the quick titration buttons, the programming code is operable to display as a next display screen, without an intervening display screen, a near view titration screen.

12. The medical pump system of claim 1 wherein the programming code is operable to display a MAIN MENU button on the near view screen; the MAIN MENU button being operable to display the far view screen as a next screen, without displaying an intervening screen, when touched by the user.

13. The medical pump system of claim 1 wherein the programming code is operable to display an EDIT button that, when activated by the user, immediately causes a near view programming screen to be displayed as a next screen without an intervening screen.

14. A medical pump system comprising:
an input device for entering one of a command and a value of a pump programming parameter;
a memory for storing programming code;
a processor in communication with the memory and the input device being operable to execute the programming code and, in response to at least one of the programming code, the command, and the value of the pump programming parameter, generate a display signal;
an output device in communication with the processor to receive the display signal and in response to the display signal generate one of a plurality of screens, the plurality of screens including a far view screen and a near view screen;
wherein the programming code is operable to display on the far view screen a plurality of medical therapy buttons, at least one of the medical therapy buttons, when activated by a user, displaying one of a near view programming screen and a plurality of quick titration buttons;
wherein one of the near view screen and the far view screen is operable to display a distal pressure button on which a first graph of distal pressure over a first time period is depicted.

15. The medical pump system of claim 14 wherein upon being activated by the user the distal pressure button is operable to cause display of a second graph of distal pressure in a size that is larger than the first graph.

16. The medical pump system of claim 15 wherein the second graph depicts distal pressure over a second time period that is greater than the first time period.

17. A medical pump system comprising:
an input device for entering one of a command and a value of a pump programming parameter;
a memory for storing programming code;
a processor in communication with the memory and the input device being operable to execute the programming code and, in response to at least one of the programming code, the command, and the value of the pump programming parameter, generate a display signal;
an output device in communication with the processor to receive the display signal and in response to the display signal generate one of a plurality of screens, the plurality of screens including a far view screen and a near view screen;
wherein the programming code is operable to display on the far view screen a plurality of medical therapy buttons, at least one of the medical therapy buttons, when activated by a user, displaying one of a near view programming screen and a plurality of quick titration buttons;
wherein one of the plurality of screens includes a fixed position button that, when touched by the user, toggles text displayed on the fixed position button and corresponding function/response to display one selection of text and corresponding function/response from a plurality of selections of text and corresponding function/response.

* * * * *